(12) United States Patent
Ali et al.

(10) Patent No.: US 11,970,509 B1
(45) Date of Patent: Apr. 30, 2024

(54) WATER SOLUBLE NANO-SIZED IMINE Ru(III) COMPLEX BASED ON 4-AMINOBENZENE SODIUM SULPHONATE FOR BIOMEDICAL APPLICATIONS

(71) Applicant: KING FAISAL UNIVERSITY, Al-Ahsa (SA)

(72) Inventors: Mai Mostafa Khalaf Ali, Al-Ahsa (SA); Hany Mohamed Abd El-Lateef Ahmed, Al-Ahsa (SA); Mohamed Gouda, Al-Ahsa (SA); Asmaa Ebrahim Hassan, Sohag (EG); Mosa Alsehli, Al-Mounawara (SA); Eida S Al-Farraj, Riyadh (SA); Ahmed M. Abu-Dief, Al-Mounawara (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 18/529,497

(22) Filed: Dec. 5, 2023

(51) Int. Cl.
| | |
|---|---|
| *C07F 15/00* | (2006.01) |
| *A61K 9/51* | (2006.01) |
| *A61P 31/04* | (2006.01) |
| *A61P 31/10* | (2006.01) |
| *A61P 35/00* | (2006.01) |
| *A61P 39/06* | (2006.01) |

(52) U.S. Cl.
CPC ............ *C07F 15/0053* (2013.01); *A61K 9/51* (2013.01); *A61P 31/04* (2018.01); *A61P 31/10* (2018.01); *A61P 35/00* (2018.01); *A61P 39/06* (2018.01)

(58) Field of Classification Search
CPC ........ C07F 15/0053; A61K 9/51; A61P 31/04; A61P 31/10; A61P 35/00; A61P 39/06
See application file for complete search history.

(56) References Cited

U.S. PATENT DOCUMENTS 11,897,902 B1 * 2/2024 El-Latef Ahmed ..... A61P 31/04

FOREIGN PATENT DOCUMENTS

CN 115850345 A 3/2023

OTHER PUBLICATIONS

Fen et al ("Science China Chemistry", Aug. 2011 vol. 54 No. 8: 1357-1364) (Year: 2011).*
PubChem 4 most similar structures to ligand structure applicants PA0001075; 2023.
PubChem most similar structure to ligand structure applicants PA0001075; 2023.
PubChem Sodium 4-aminobenzenesulfonate_C6H6NNaO3S_CID 23664644—PubChem; 2023.
Suleyman Akocak et al.; "Synthesis and biological evaluation of novel aromatic and heterocyclic bis-sulfonamide Schiff bases as carbonic anhydrase I, II, VII and IX inhibitors"; Bioorganic & Medicinal Chemistry vol. 25, Issue 12, Jun. 15, 2017, pp. 3093-3097.
Ahmed M. Abu-Dief et al.; "A review on versatile applications of transition metal complexes incorporating Schiff bases"; Beni Suef Univ J Basic Appl Sci. Jun. 2015; 4(2): 119-133. Published online May 16, 2015. doi: 10.1016/j.bjbas.2015.05.004.
Abebe, Atakilt, and Tizazu Hailemariam. "Synthesis and assessment of antibacterial activities of ruthenium (III) mixed ligand complexes containing 1, 10-phenanthroline and guanide." Bioinorganic chemistry and applications 2016 (2016).

* cited by examiner

*Primary Examiner* — Jean P Cornet
(74) *Attorney, Agent, or Firm* — Nath, Goldberg & Meyer; Richard C. Litman

(57) ABSTRACT

A imine Ru(III) complex based on 4-Aminobenzene Sodium Sulphonate, its synthesis, and its use for pharmaceutical applications.

15 Claims, 1 Drawing Sheet

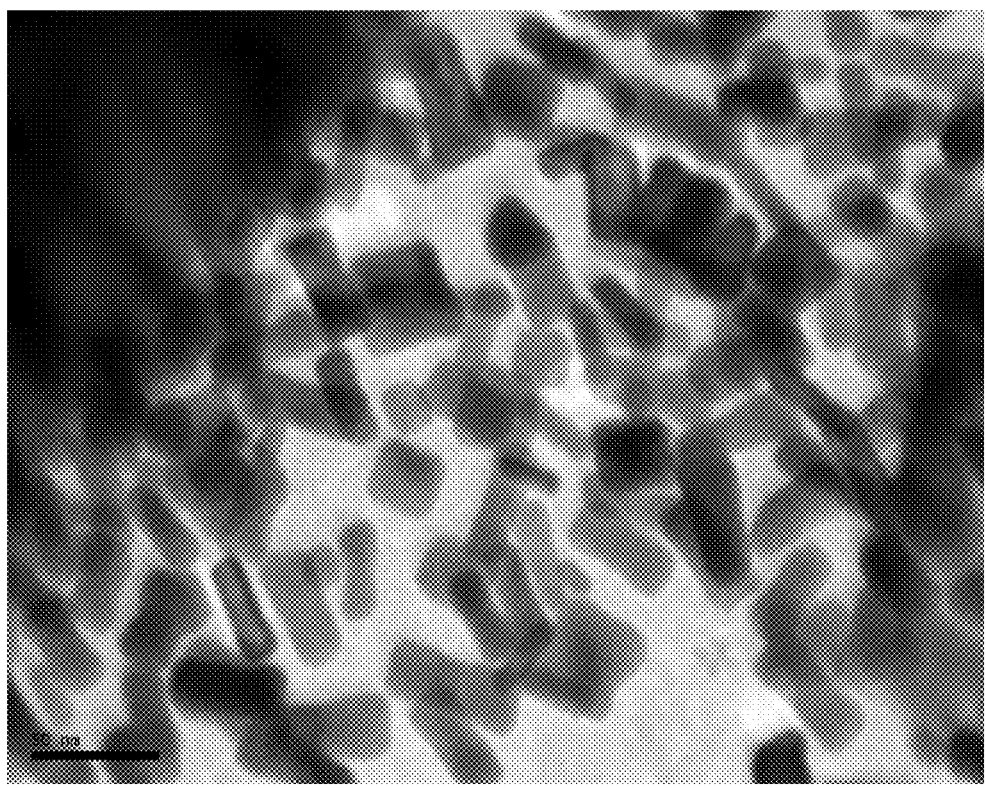

WATER SOLUBLE NANO-SIZED IMINE Ru(III) COMPLEX BASED ON 4-AMINOBENZENE SODIUM SULPHONATE FOR BIOMEDICAL APPLICATIONS

BACKGROUND

1. Field

The present disclosure relates to a novel nano-sized imine Ru(III) complex based on 4-Aminobenzene Sodium Sulphonate, its synthesis, and its use for potential medicinal applications.

2. Description of the Related Art

Over recent decades, the supramolecular chemistry has become a matter of interest. The design and development of new biomaterials and the molecular frameworks have increased rapidly, addressing the coordination chemistry of biologically active chelates.

Due to their excellent antimicrobial and anticancer properties, transition metal complexes with Schiff base ligands are an active research area and Schiff base compounds have received a lot of attention from researchers.

Schiff bases are useful in many different areas such as polymer stabilizers, catalysts, intermediates in organic synthesis, dyes, and pigments. Furthermore, Schiff bases are an essential class of ligands in coordination chemistry. Schiff bases have also been demonstrated to have antibacterial, antifungal, antimalarial, antiviral, anti-inflammatory, and antipyretic effects, among other biological activities. The creation of novel compounds with unique physical, chemical, and biological properties results from the synthesis of nano-sized complexes. The 1st row of transition metal chelates has numerous uses in various domains. Specifically, prepared nano-sized mixed ligand with Ru(III) complexes may have superior pharmaceutical applications compared to standard drugs.

On the other hand, cancer is a disease that is killing millions of people worldwide, and the design of small molecules (metal-based drugs) that bind and react at specific sequences with circulating tumor (ct-DNA) are especially important in the development of new therapeutic reagents.

Thus, new nano-sized mixed ligand molecules having desired therapeutic activities and solving the aforementioned problems are desired.

SUMMARY

The present subject matter relates to a novel nano-sized imine Ru(III) complex based on 4-Aminobenzene Sodium Sulphonate, its synthesis, and its use for potential medicinal applications.

The investigated imine ligand derived from Phethaldehyde and 4-Aminobenzene Sodium Sulphonate can be synthesized as described herein. The Schiff base ligand can be used to synthesize novel nano complex with $RuCl_3 \cdot 3H_2O$. The prepared ligand and nano Ru(III) complex can be deduced by different spectroscopic techniques. The nano-sized Ru(III) complex can be synthesized in an environmentally friendly manner. The structure, morphologies and particle size of the nano-sized complexes were determined using FT-IR, TEM, and PXRD. The results displayed that the nano-domain chelate is on the sub-nano scale. Experimental data were supported by DFT calculations. The findings revealed that the nano-metal complexes investigated are more stable than the studied free ligand.

In an embodiment, the present subject matter relates to an imine Ru(III) complex based on 4-Aminobenzene Sodium Sulphonate having the formula I:

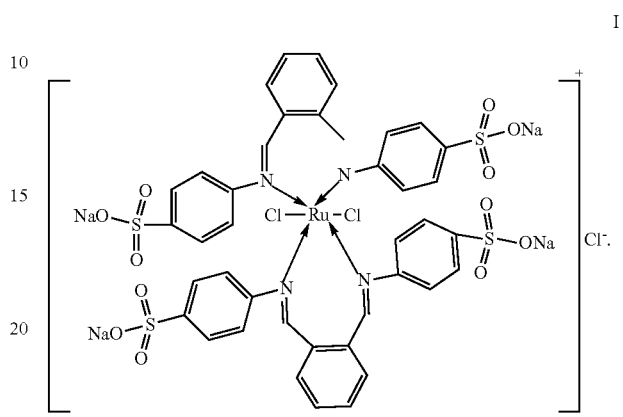

In another embodiment, the present subject matter relates to a pharmaceutically acceptable composition comprising a therapeutically effective amount of the imine Ru(III) complex based on 4-Aminobenzene Sodium Sulphonate and a pharmaceutically acceptable carrier.

In a further embodiment, the present subject matter relates to a method of treating cancer in a patient comprising administering to a patient in need thereof a therapeutically effective amount of the imine Ru(III) complex based on 4-Aminobenzene Sodium Sulphonate as described herein.

In an embodiment, the present subject matter relates to a method of treating a microbial infection in a patient, comprising administering to a patient in need thereof a therapeutically effective amount of the imine Ru(III) complex based on 4-Aminobenzene Sodium Sulphonate as described herein.

In another embodiment, the present subject matter relates to a method of promoting an antioxidant effect in a patient, comprising administering to a patient in need thereof a therapeutically effective amount of the imine Ru(III) complex based on 4-Aminobenzene Sodium Sulphonate as described herein.

In a further embodiment, the present subject matter relates to a method of making the imine Ru(III) complex based on 4-Aminobenzene Sodium Sulphonate as described herein, the method comprising: adding a solution of Ruthenium (III) chloride ($RuCl_3$) in water to a phethaldehyde and 4-Aminobenzene Sodium Sulphonate ligand in water to obtain a mixture; sonicating the mixture; and obtaining the imine Ru(III) complex based on 4-Aminobenzene Sodium Sulphonate as described herein.

These and other features of the present subject matter will become readily apparent upon further review of the following specification.

BRIEF DESCRIPTION OF THE DRAWINGS

The sole FIGURE shows a TEM image of the prepared water soluble nano-sized imine Ru(III) complex based on 4-Aminobenzene Sodium Sulphonate ligand.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer, a microbial infection, or an oxidant related condition.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to an imine Ru(III) complex based on 4-Aminobenzene Sodium Sulphonate ligand having the formula I:

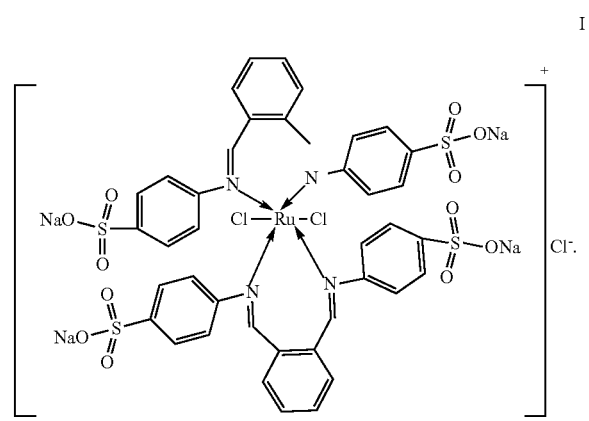

In certain embodiments, the complex can be formed as nanoparticles. In other embodiments, the nanoparticles can be water soluble. In further embodiments, the nanoparticles can have an average size of about 34 nm to about 39 nm, about 34 nm, about 35 nm, about 36 nm, about 37 nm, about 38 nm, or about 39 nm. Since the present complex is itself nanosized, it does not need to be loaded onto other particles to increase its activity. Further, in an embodiment, the size of the complex directly, favorably affects its uses for super pharmaceutical applications.

In another embodiment, the present subject matter relates to a pharmaceutically acceptable composition comprising a therapeutically effective amount of the imine Ru(III) complex based on 4-Aminobenzene Sodium Sulphonate ligand and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for cancer, a microbial infection, or an oxidant related condition. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of cancer, a microbial infection, or an oxidant related condition, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

The present compounds have valuable pharmaceutical properties, which make them commercially utilizable. Accordingly, the present subject matter further relates to use of the present compounds for the treatment of diseases such as cancers.

Accordingly, in a further embodiment, the present subject matter relates to a method of treating cancer in a patient comprising administering to a patient in need thereof a therapeutically effective amount of the imine Ru(III) complex based on 4-Aminobenzene Sodium Sulphonate ligand as described herein.

In an embodiment, the cancer is breast cancer.

In another embodiment of the present subject matter, the present complex demonstrated in vitro anticancer action against a human breast cancer cell line. Accordingly, the present subject matter relates to methods of treating a cancer in a patient by administering the complex presented herein to a patient in need thereof.

In one embodiment, a present complex engaged for in vitro study against a breast cancer cell line can display an $IC_{50}$ concentration of about 1.50 µg/ml.

In a further embodiment, the present subject matter relates to a method of treating a microbial infection in a patient, comprising administering to a patient in need thereof a therapeutically effective amount of the imine Ru(III) complex based on 4-Aminobenzene Sodium Sulphonate ligand as described herein.

In an embodiment, the microbial infection is caused by one or more of *E. coli*, and *Aspergillus flavus*.

In an embodiment, a present complex engaged for in vitro study against *E. coli* can display an inhibition zone of about 50 mm and an MIC of about 0.50 µg/ml.

In a further embodiment, a present complex engaged for in vitro study against *Aspergillus flavus* can display an inhibition zone of about 40 mm and an MIC of about 1.25 µg/ml.

In another embodiment, the present subject matter relates to a method of promoting an antioxidant effect in a patient, comprising administering to a patient in need thereof a therapeutically effective amount of the 4-bromo-2-(quinolin-2-yliminomethyl)-phenol imine]-Ru(III)-phenanthroline complex as described herein.

In one embodiment, a present complex engaged for in vitro study as an antioxidant can display an $IC_{50}$ concentration of 5.5 µg/ml.

The present subject matter further relates to a method of treating or preventing a disease comprising administering to a patient in need thereof a therapeutically effective amount of the complex herein.

In the above methods, the patient is preferably a mammal, more preferably a human. In an embodiment, the present complex can be used in combination therapy with one or more additional active agents.

In a further embodiment, the present subject matter relates to a method of making the imine Ru(III) complex based on 4-Aminobenzene Sodium Sulphonate as described herein, the method comprising: adding a solution of Ruthenium (III) chloride ($RuCl_3$) in water to a phethaldehyde and 4-Aminobenzene Sodium Sulphonate ligand in water to obtain a mixture; sonicating the mixture; and obtaining the imine Ru(III) complex based on 4-Aminobenzene Sodium Sulphonate as described herein.

In an embodiment of the present production methods, the imine Ru(III) complex based on 4-Aminobenzene Sodium Sulphonate can be obtained as a nanosized complex. Further, the 4-Bromo-2-[(9H-purin-6-ylimino)-methyl]-phenol imine Pd(II) complex can be obtained as a dark violet crystalline powder.

In an embodiment, the mixture is sonicated for at least about 60 minutes, at least 60 minutes, or about 60 minutes.

In yet another embodiment of the present production methods, the $RuCl_3$ solution is added stepwise.

In a still another embodiment of the present production methods, wherein the $RuCl_3$ and the ligand are mixed in about a 1:2 molar ratio.

The following examples relate to various methods of manufacturing the specific compounds and application of the same, as described herein. All compound numbers expressed herein are with reference to the synthetic pathway figures shown above.

EXAMPLES

Example 1

Preparation of imine Ru(III) complex based on 4-Aminobenzene Sodium Sulphonate)

A solution of $RuCl_3$ (2 mmol, 0.415 g) in water as added stepwise to the investigated ligand (1.95 g, 4 mmol) in water and the mixture was subjected to sonication for 60 minutes, then a dark violet crystalline powder of nanosized complex was obtained.

Characterization of the prepared nano-complex using TEM analysis is shown in the sole FIGURE. The prepared complex is a nanoparticle which can be water soluble. According to the TEM image, the average size of the prepared nano complex is 34-39 nm. This affects directly on the super medicinal/biomedical application of the prepared complex.

Example 2

Antimicrobial Activity—E. coli

To evaluate antimicrobial activity, the bacterial strain *Escherichia coli*(-ve), was used. These strains cultured in nutrient agar and Muller-Hinton medium. Ofloxacin compounds were used as a standard drug for comparison.

The susceptibilities of such growth rate of microorganisms were measured in vitro by agar well diffusion method. The tested nano complex was dissolved in dimethylsulfoxide at different concentrations (10 and 20 mg/ml). 1 $cm^3$ of a 24 h broth culture containing $10^6$ $CFU/cm^3$ was placed in sterile Petri-dishes. Molten nutrient agar (15 $cm^3$) maintained at 45° C. was then poured into the Petri-dishes and allowed to solidify. Then holes of 6 mm diameter were formed in the agar using a sterile cork borer and these holes were completely filled with the test solutions. The plates were incubated for 24 h at 37° C. After the incubation period, the zone of inhibition of each well was determined by measuring the zones of growth inhibition (mm) against the test microorganisms with zone reader (Hi Antibiotic zone scale). In order to clarify the effect of solvent (DMSO) on the biological screening, DMSO alone was used as control, and it showed no activity against microbial strains. The measurements were made in triplicate for each compound and their average values are reported.

The prepared water soluble nano complex showed potent antibacterial activity against *E. coli* bacteria with an inhibition zone of 50 mm and an MIC of 0.50 μg/ml compared with the standard drug Ofloxacin (38 mm and MIC 2.5 μg/ml).

Example 3

Antifungal Activity—Aspergillus flavus

To evaluate antimicrobial activity, the fungal strain (*Aspergillus flavus*), was used. These strains cultured in nutrient agar and Muller-Hinton medium. Fluconazole compounds were used as a standard drug for comparison.

Antifungal activities of the prepared water soluble nanocomplex were studied against three fungal cultures using well diffusion method. The tested fungi were inoculated in Sabouraud dextrose broth medium (Hi-Media Mumbai) and incubated at 35° C. for 72 h and subsequently a suspension of about $1.60\times10^4$-$6.00\times10^4$ c.f.u/ml was introduced agar plates and a sterile glass spreader was used for even distribution of the inoculum. The discs measuring 6 mm in diameter were prepared from Whatman No. 1 filter paper and sterilized by dry heat at 140° C. for 1 h. The sterile discs previously soaked in known concentration of the tested compounds were placed in Sabouraud dextrose Agar (SDA) plates. The plates were inverted and incubated at 35° C. for 7 days. The susceptibility was assessed on the basis of diameter of inhibition against *albicans* and non-albicans strain of fungi.

The prepared complex showed enhanced activity against *Aspergillus flavus* fungi with an inhibition zone of 40 mm and an MIC of 1.25 μg/ml compared with the standard drug Fluconazol (28 mm and MIC 1.75 μg/ml).

Example 4

Anti-Cancer Activity—Breast Cancer

The anticancer activity was made at the National Cancer Institute, Cancer Biology Department, Pharmacology Department, Cairo University. The absorbance or optical density (O.D.) of each well was measured spectrophotometrically at 564 (nm) with an "ELIZA" micro plate reader (Meter tech. Σ 960, "USA"). Evaluation of the cytotoxic activity of the prepared nano-complex was carried out against Breast cancer cells line. The evaluation process was carried out in vitro using the Sulfo-Rhodamine-B-stain (SRB). Cells were placed in 96-multiwell plate ($10^4$ cells/well) for 24 hours before processing with the complexes to allow attachment of cell to the wall of the plate. Various concentrations of the compounds under test in DMSO (0, 1, 2.5, 5 and 10 μM) were added to the cell monolayer. Monolayer cells were incubated with the complexes for 48 hours at 37° C. and in atmosphere of 5% $CO_2$. After 48 hours, cells were fixed, rinsed, and stained with Sulfo-Rhodamine-B-stain. Excess stain was washed with acetic acid and attached stain was treated with Tris EDTA buffer. Color intensity was measured in an ELISA reader. $IC_{50}$ was evaluated and potency was calculated with regard to percentage of change of (vistabline standard). The relation between surviving fraction and compound concentration is plotted to get the survival curve of each tumor cell line after the specified compound. The experiment was carried out once and each concentration repeated 3 times.

The inhibitory concentration percent (IC %) was estimated according to the equation: Inhibition concentration:

(IC) %=(Control O.D.×Ligand O.D.)×100/Control O.D

The prepared complex showed super anticancer activity with an $IC_{50}$ of 1.50 μg/μl against a breast cancer cell line compared with the Doxorubicin standard drug ($IC_{50}$=4.00 μg/μl).

Example 5

Antioxidant Activity

In vitro antioxidant activity of the newly nano complex was evaluated using scavenging the stable DPPH radical modified method. The model of scavenging the stable DPPH radical is a method that is widely used to evaluate antioxidant activities in a relatively short time compared with other methods. DPPH' radical scavenging test relies on the absorbance change of the radical when deactivated by antioxidants, which easily observable with naked eye as color changes from purple to yellow. Stock solutions of the investigated compounds were dissolved in methanol-DMSO (4:1) was diluted to final concentration of 10, 25, 50, 100 and 150 M. Methanolic DPPH (2,2-diphenyl-1-picrylhydrazyl) solution (1 mL, 0.3 mmol) was added to 3.0 mL of the synthesized compounds as well as standard compound (Ascorbic acid). The tube was protected from light by covering with aluminum foil and the absorbance was measured at 517 nm after 30 min. using methanol as a blank. All the tests were made in triplicates. Vitamin C was used as standard or positive control, parallel to the test compound and in the absence of the test compound/standard used as the negative control. The reduction in the absorbance of DPPH was calculated relative to the measured absorbance of the control. Lower absorbance values of reaction mixture indicated higher free-radical-scavenging activity. The percentage of DPPH radical scavenging activity was calculated using the below equation:

$$\% \; DPPH \; \text{scavenging activity} = \frac{A_C - A_S}{A_C}$$

where $A_C$ is the absorbance of the L-ascorbic acid (Standard) and $A_S$ is the absorbance of different compounds. The methanolic DPPH solution (1 mL, 0.3 mM) was used as control. The effective concentration of sample required to scavenge DPPH radical by 50% ($IC_{50}$ value) was obtained by linear regression analysis of dose-response curve plotting between % inhibition and concentrations.

The prepared complex showed super antioxidant activity with an $IC_{50}$ of 5.5 µg/µl compared with the l-ascorbic acid standard antioxidant ($IC_{50}$=45.5 µg/µl).

It is to be understood that the imine Ru(III) complex based on 4-Aminobenzene Sodium Sulphonate is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A imine Ru(III) complex based on 4-Aminobenzene Sodium Sulphonate having the formula I:

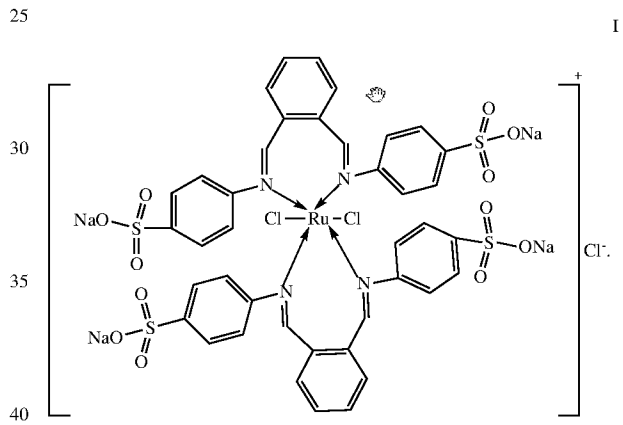

2. The imine Ru(III) complex based on 4-Aminobenzene Sodium Sulphonate of claim 1, wherein the complex is formed as nanoparticles.

3. The imine Ru(III) complex based on 4-Aminobenzene Sodium Sulphonate of claim 2, wherein the nanoparticles are water soluble.

4. The imine Ru(III) complex based on 4-Aminobenzene Sodium Sulphonate of claim 2, wherein the nanoparticles have an average size of about 34 nm to 39 nm.

5. The imine Ru(III) complex based on 4-Aminobenzene Sodium Sulphonate of claim 2, wherein the nanoparticles have an average particle size of about 36 nm.

6. A pharmaceutically acceptable composition comprising a therapeutically effective amount of the imine Ru(III) complex based on 4-Aminobenzene Sodium Sulphonate of claim 1 and a pharmaceutically acceptable carrier.

7. A method of treating a microbial infection caused by one or more of *E. coli* and *Aspergillus flavus* in a patient comprising administering to a patient in need thereof a therapeutically effective amount of an imine Ru (III) complex based on 4-Aminobenzene Sodium Sulphonate having the formula I:

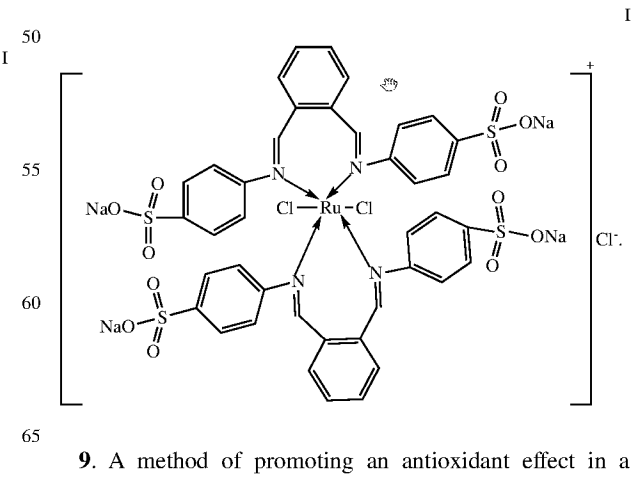

8. A method of treating breast cancer in a patient comprising administering to a patient in need thereof a therapeutically effective amount of a imine Ru (III) complex based on 4-Aminobenzene Sodium Sulphonate having the formula I:

9. A method of promoting an antioxidant effect in a patient, comprising administering to a patient in need thereof a therapeutically effective amount of a imine Ru (III) complex based on 4-Aminobenzene Sodium Sulphonate having the formula I:

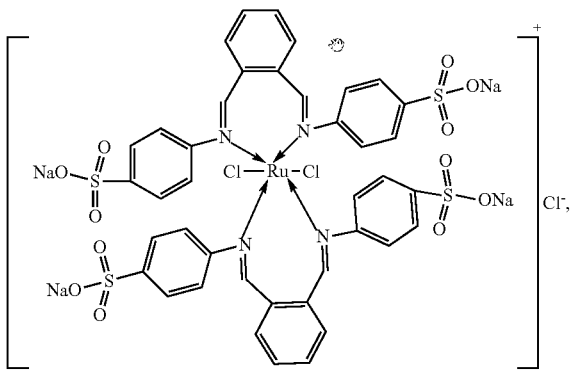

wherein the patient is a patient having breast cancer, *E. coli*, or *Aspergillus Flavus*.

10. A method of making the imine Ru(III) complex based on 4-Aminobenzene Sodium Sulphonate of claim 1, the method comprising:

adding a solution of Ruthenium (III) chloride ($RuCl_3$) in water to a phethaldehyde and 4-Aminobenzene Sodium Sulphonate ligand in water to obtain a mixture;

sonicating the mixture; and obtaining the imine Ru(III) complex based on 4-Aminobenzene Sodium Sulphonate.

11. The method of making the imine Ru(III) complex based on 4-Aminobenzene Sodium Sulphonate of claim 10, wherein the $RuCl_3$ is added stepwise.

12. The method of making the imine Ru(III) complex based on 4-Aminobenzene Sodium Sulphonate of claim 10, wherein the mixture is sonicated for at least about 60 minutes.

13. The method of making the imine Ru(III) complex based on 4-Aminobenzene Sodium Sulphonate of claim 10, wherein the $RuCl_3$ and the ligand are mixed in about a 1:2 molar ratio.

14. The method of making the imine Ru(III) complex based on 4-Aminobenzene Sodium Sulphonate of claim 10, wherein the imine Ru(III) complex based on 4-Aminobenzene Sodium Sulphonate is a dark violet crystalline powder.

15. The method of making the imine Ru(III) complex based on 4-Aminobenzene Sodium Sulphonate of claim 10, wherein the imine Ru(III) complex based on 4-Aminobenzene Sodium Sulphonate is a nanosized complex.

* * * * *

UNITED STATES PATENT AND TRADEMARK OFFICE
CERTIFICATE OF CORRECTION

| | | |
|---|---|---|
| PATENT NO. | : 11,970,509 B1 | |
| APPLICATION NO. | : 18/529497 | |
| DATED | : April 30, 2024 | |
| INVENTOR(S) | : Mai Mostafa Khalaf Ali et al. | |

It is certified that error appears in the above-identified patent and that said Letters Patent is hereby corrected as shown below:

On the Title Page

Item (72) Inventors, please delete the fifth and seventh Inventor city "Al-Mounawara" and replace with "Al-Madina Al-Mounawara".

Signed and Sealed this
Twenty-eighth Day of May, 2024

Katherine Kelly Vidal
*Director of the United States Patent and Trademark Office*